United States Patent [19]

Hughes et al.

[11] Patent Number: 5,363,856
[45] Date of Patent: Nov. 15, 1994

[54] CORRECTING THERMAL DRIFT IN CARDIAC OUTPUT DETERMINATION

[75] Inventors: Timothy J. Hughes, Palo Alto, Calif.; David N. Swingler, Halifax, Nova Scotia, Canada

[73] Assignee: Abbott Laboratories, Abbott Park, Ill.

[21] Appl. No.: 106,206

[22] Filed: Aug. 13, 1993

[51] Int. Cl.$^5$ .............................................. A61B 5/029
[52] U.S. Cl. ...................................... 128/713; 128/736
[58] Field of Search ................................ 128/713, 736

[56] References Cited

U.S. PATENT DOCUMENTS

| | | | |
|---|---|---|---|
| 4,236,527 | 12/1980 | Newbower et al. | 128/692 |
| 4,507,974 | 4/1985 | Yelderman | 73/861.06 |
| 4,745,928 | 5/1988 | Webler et al. | 128/692 |
| 4,819,655 | 4/1989 | Webler | 128/713 |
| 5,261,411 | 11/1993 | Hughes | 128/713 |

FOREIGN PATENT DOCUMENTS

WO91/16603 10/1991 WIPO.

OTHER PUBLICATIONS

J. H. Philip et al., "Continuous Thermal Measurement of Cardiac Output," Transactions On Biomedical Engineering, vol. BME-31, No. 5, May 1984, pp. 393–400.

*Primary Examiner*—William E. Kamm
*Assistant Examiner*—Kennedy J. Schaetzle
*Attorney, Agent, or Firm*—Christensen, O'Connor, Johnson & Kindness

[57] ABSTRACT

A method and apparatus for correcting thermal drift in cardiac output measurements based upon a temperature signal indicative of the change in temperature of blood leaving the heart is disclosed. In a first preferred embodiment of a cardiac output monitoring system(10), the catheter(14) is provided with an electrical resistance heater (22). An electrical current having a sinusoidal waveform with a period of from 30 to 60 seconds is applied to the heater, causing power to be dissipated into the blood within a patient's heart (12). A temperature sensor (24) disposed near a distal end of the catheter produces a signal indicative of the temperature of blood leaving the heart. The temperature signal and the signal corresponding to the electrical power dissipated in the heater (an input signal) are filtered at a frequency $\omega$ corresponding to the frequency of the applied electrical current, i.e., the frequency of the input signal. An output signal indicative of the temperature of the blood leaving the heart, corrected for the effects of thermal drift, is then determined. The corrected cardiac output signal is determined by first determining a drift slope of the blood temperature signal due to thermal drift. The drift slope is then used to produce a signal corrected for thermal drift. Cardiac output is determined as a function of the amplitude of the input power, the amplitude of the signal corrected for thermal drift, and their phase difference.

25 Claims, 3 Drawing Sheets

CORRECTING THERMAL DRIFT IN CARDIAC OUTPUT DETERMINATION

FIELD OF THE INVENTION

The present invention relates to methods and apparatus for correcting for thermal drift in cardiac output determinations.

BACKGROUND OF THE INVENTION

Cardiac output, the volumetric rate at which blood is pumped through the heart, is most often determined clinically by injecting a bolus of chilled saline or glucose solution into the right auricle or right ventricle through a catheter. A thermistor disposed in the pulmonary artery is used to determine a temperature-time washout curve as the chilled injectate/blood mixture is pumped from the heart. The area under this curve provides an indication of cardiac output. Although this thermo-dilution method can give an indication of cardiac output at the time the procedure is performed, it cannot be used for continuously monitoring cardiac output. Moreover, the frequency with which the procedure is performed is limited by its adverse effects on a patient, including the dilution of the patient's blood that occurs each time the chilled fluid is injected. In addition, the procedure poses an infection hazard to medical staff from blood contact, and to the patient, from exposure to possibly contaminated injectate fluid or syringes.

Alternatively, blood in the heart can be chilled or heated in an injectateless method by a heat transfer process using a temperature-conditioned fluid that is pumped in a closed loop, toward the heart through one lumen within the catheter and back through another lumen. The principal advantages of using such a non-injectate heat transfer process to change the temperature of blood are that repetitive measurements can be performed without overloading the patient with large quantities of fluid or exposing the patient to the risk of infection.

U.S. Pat. No. 4,819,655 (Webler) discloses an injectateless method and apparatus for determining cardiac output. In Webler's preferred embodiment, a saline solution is chilled by a refrigeration system or ice bath and introduced into a catheter that has been inserted through a patient's cardiovascular system into the heart. The catheter extends through the right auricle and right ventricle and its distal end is disposed just outside the heart in the pulmonary artery. A pump forces the chilled saline solution through a closed loop fluid path defined by two lumens in the catheter, so that heat transfer occurs between the solution and blood within the heart through the walls of the catheter. A thermistor disposed at the distal end of the catheter monitors the temperature of blood leaving the heart, both before the chilled fluid is circulated through the catheter to define a baseline temperature, and after the temperature change in the blood due to heat transfer with the chilled saline solution has stabilized. Temperature sensors are also provided to monitor both the temperature of the chilled saline solution at or near the point where it enters the catheter (outside the patient's body) and the temperature of the fluid returning from the heart. In addition, the rate at which the chilled solution flows through the catheter is either measured or controlled to maintain it at a constant value. Cardiac output (CO) is then determined from the following equation:

$$CO = \frac{\dot{V}_I \cdot (\Delta T_I)}{C \cdot (\Delta T_B)} \quad (1)$$

where
- $\dot{V}_I$ equals the rate at which the chilled fluid is circulated through the catheter;
- $\Delta T_I$ equals the difference between the temperature of the chilled fluid input to the catheter and the temperature of the fluid returning from the heart;
- $\Delta T_B$ equals the difference between the temperature of the blood leaving the heart before the chilled fluid is circulated and the temperature of the blood leaving the heart after the chilled fluid is circulated (after the temperature stabilizes); and
- C is a constant dependent upon the blood and fluid properties. The patent also teaches that the fluid may instead be heated so that it transfers heat to the blood flowing through the heart rather than chilled to absorb heat.

U.S. Pat. No. 4,819,655 further teaches that the cardiac monitoring system induces temperature variations in the pulmonary artery that are related to the patient's respiratory cycle and are therefore periodic at the respiratory rate. Accordingly, Webler suggests that the signal indicative of $T_B'$ (the temperature of the chilled blood exiting the heart) should be processed through a Fourier transform to yield a period and amplitude for the respiratory cycle, the period or multiples of it then being used as the interval over which to process the data to determine cardiac output.

Another problem recognized by Webler is the delay between the times at which circulation of the chilled fluid begins and the temperature of the blood in the pulmonary artery reaches equilibrium, which is caused by the volume of blood surrounding the catheter in the right ventricle and in other portions of the heart. The patent suggests introducing a generally corresponding delay between the time that temperature measurements are made of the blood before the chilled fluid is circulated and after, for example, by waiting for the $T_B'$ value to exceed a level above that induced by respiratory variations. However, for a relatively large volume heart and/or very low cardiac output, the $T_B'$ data do not reach equilibrium in any reasonable period of time. The quantity of blood flowing through the large volume heart represents too much mixing volume to accommodate the technique taught by Webler for processing the data to determine cardiac output. As a result, the measurement period for equilibrium must be excessively long to reach equilibrium, thereby introducing a potential error in the result due to either a shift in the baseline temperature of the blood or changes in the cardiac output. For this reason, the technique taught by Webler to determine cardiac output using the data developed by his system is not practical in the case of large blood volumes in the heart and/or low cardiac outputs.

Instead of cooling (or heating) the blood in the heart by heat transfer with a circulating fluid to determine cardiac output, the blood can be heated with an electrical resistance heater that is disposed on a catheter inserted into the heart. The apparatus required for this type of injectateless cardiac output measurement is significantly less complex than that required for circulating a fluid through the catheter. An electrical current is applied to the resistor through leads in the catheter and adjusted to develop sufficient power dissipation to produce a desired temperature rise signal in the blood. However, care must be taken to avoid using a high power that might damage the blood by overheating it. An adequate signal-to-noise ratio is instead preferably obtained by applying the electrical current to the heater at a frequency corresponding to that of the minimum noise generated in the circulatory system, i.e., in the range of 0.02 through 0.15 Hz. U.S. Pat. No. 4,236,527 (Newbower et al.) describes such a system, and more importantly, describes a technique for processing the signals developed by the system to compensate for the above-noted effect of the mixing volume in the heart and cardiovascular system of a patient, even one with a relatively large heart. (Also see J. H. Philip, M. C. Long, M. D. Quinn, and R. S. Newbower, "Continuous Thermal Measurement of Cardiac Output," IEEE Transactions on Biomedical Engineering, Vol. BMI 31, No. 5, May 1984.)

Newbower et al. teaches modulating the thermal energy added to the blood at two frequencies, e.g., a fundamental frequency and its harmonic, or with a square wave signal. Preferably, the fundamental frequency equals that of the minimal noise in the cardiac system. The temperature of the blood exiting the heart is monitored, producing an output signal that is filtered at the fundamental frequency to yield conventional cardiac output information. The other modulation frequency is similarly monitored and filtered at the harmonic frequency, and is used to determine a second variable affecting the transfer function between the injection of energy into the blood and the temperature of the blood in the pulmonary artery. The amplitude data developed from the dual frequency measurements allow the absolute heart output to be determined, thereby accounting for the variability of fluid capacity or mixing volume.

Newbower's technique for determining cardiac output requires the use of a model for the system represented by the effect of the input power on the blood temperature output signal. The data must be fit to the model to correct for mixing volume attenuation.

As an alternative to the model of Newbower, M. Yelderman has developed a method for reconstructing an impulse response for a cardiac output monitoring system using a pseudo random binary noise and cross correlation technique. This method is described in U.S. Pat. No. 4,507,974. Yelderman teaches that any indicator may be introduced in the blood mass in the form of a stochastic or spread spectral process. For example, a catheter mounted heating filament can be energized with a stochastic or pseudo random input to supply a corresponding heat input signal to the blood in the heart. The vascular system impulse response obtained by downstream measurement and cross correlation with the input signal produces information that is then combined with a conservation of heat equation to measure volumetric fluid flow by integrating the area under the impulse response curve. Yelderman's method is prone to drift and noise being coupled into the reconstructed impulse response, which makes accurate level detection and integration difficult.

One inaccuracy in prior art methods of determining cardiac output is due to thermal noise and thermal drift. Thermal drift is generally a very low frequency drift in the temperature of the blood in the heart and is due to physiological factors as opposed to the thermal energy introduced into the blood during cardiac output measurements.

One cause of thermal noise is the difference in temperature between the blood returning from different parts of the body. Fluctuating pressure gradients across the chest wall caused by respiration vary the volume of blood returning to the heart from organs outside the chest relative to the volume of blood returning from organs inside the chest. Blood returning from organs with a high metabolic rate such as the liver is hotter than blood returning from, e.g., the stomach, while blood returning from the peripheral pans of the body is much colder, depending partly on room temperature. As blood returns from different parts of the body, the temperature of the blood in the heart fluctuates, thus producing a thermal noise or thermal drift in cardiac output measurements. For example, the amount of blood entering the heart from the superior or inferior vena cava varies during each respiration cycle, thus changing the temperature of the blood in the heart. Also, long term homeostatic control systems in the body cause long term, slow fluctuations in mixed venous blood temperature as a result of adjusting the quantity of blood flowing to the body's periphery and varying the metabolic rate to try to maintain "core" temperature constant.

PCT patent WO 91/16603 (McKown) discloses a method that attempts to account for the effects of thermal drift on cardiac output measurements using Yelderman's cross-correlation technique. McKown assumes that, regardless of thermal noise or drift, the average power supplied to the blood over each measurement period and thus the average power measured during cardiac output measurements remains constant. Based on this assumption, McKown determines the average level of the resultant measured temperature signal over each of several adjacent measurement periods. In the preferred embodiment, McKown uses three measurement periods, thus producing three measurements of average signal level. A quadratic curve is then fit to the data produced by measurements of average signal level. The portion of the quadratic curve associated with the center measurement period is then subtracted from the measured cardiac output signal on a point-by-point basis in order to produce "zero mean" data, thus reducing the effects of thermal drift.

McKown's method of fitting a quadratic curve to the temperature signal fits three variables simultaneously to the noisy data. If the temperature signal is particularly noisy, such a quadratic fit can induce errors larger than those present in the uncompensated original signal. McKown's method requires at least two adjacent measurement periods to be completed prior to accounting for the effect of thermal drift. If the quadratic fit is inaccurate due to short term noise during one measurement period, errors in output measurements due to that noisy period propagate to adjacent measurement periods as well, since the quadratic fit is repeated for each period using overlapping adjacent averages. This approach results in three inaccurate measurements instead of one. In addition, because McKown's method requires at least three measurement periods to be completed before cardiac output can be determined, there is a longer lag time between the occurrence of the cardiac event being measured and subsequent data output. This lag time prevents an operator from observing the cardiac output in real time, possibly affecting the patient's treatment. Due to measurement errors induced by signal-to-noise ratios and attenuation, the measurement time period cannot generally be reduced much below 30 seconds. Thus, the results of a cardiac output measurement produced by the method of McKown would be delayed by an additional one and perhaps, up to two minutes after the cardiac event.

A goal of the present invention is to provide a method and apparatus for reducing the effects of thermal drift on measurements of cardiac output while reducing some of the problems associated with the prior art, including shortening the lag time required to determine cardiac output.

SUMMARY OF THE INVENTION

The present invention corrects for the effects of thermal drift on cardiac output measurements. A blood temperature output signal indicative of the temperature of the blood flowing through the heart is determined. The slope of the output signal due to thermal drift is calculated and subsequently used to produce an output signal with a reduced dependence on thermal drift. The cardiac output is then determined as a function of the output signal with a reduced dependence on thermal drift.

The present invention allows correction for thermal drift in the output signal to be achieved within a single measurement period, i.e., in one-third the time required by the prior art technique, to correct for the effects of thermal drift. Thus, the present invention provides an operator with a measurement of cardiac output faster than prior art methods. This faster determination allows the operator to follow the cardiac event substantially on a real time basis, thus allowing the patient to be more accurately monitored during critical medical procedures.

Correction for thermal drift in a single measurement period, as provided by the present invention, also prevents errors in one measurement period from affecting output measurements in other measurement periods. In addition, the present invention uses a least mean square fit, thereby reducing inaccuracies introduced in the prior art method that are produced by using a quadratic curve fit to averaged data.

In one embodiment of the present invention, a method for determining a cardiac output of a heart with reduced dependence on thermal drift is provided that includes the step of providing an input signal to modify the temperature of the blood within the heart so that it varies periodically. A sensor that monitors the temperature of the blood leaving the heart is provided in order to produce a blood temperature output signal that varies periodically. The slope of the blood temperature output signal due to thermal drift is then determined by filtering a portion of an output signal affected by a change in the temperature of the blood caused by the input signal. This slope is used to correct the output signal so that it exhibits a reduced dependence on thermal drift. Finally, the cardiac output is determined as a function of the corrected output signal and is thus corrected for the thermal drift In accordance with another aspect of the present invention, the drift slope of the modified signal is determined by performing a least mean square fit of the signal in accordance with the following equation:

$$\text{Drift Slope} = \frac{\sum_{k4=0}^{N/4-1} [S_{k4} - T_{mean}] \cdot \left[ k4 - \frac{N}{8} + 0.5 \right]}{\sum_{k4=0}^{N/4-1} \left[ k4 - \frac{N}{8} + 0.5 \right]^2} \quad (2)$$

where:

$$S_{k4} = \frac{[T_{k4} + T_{k4+N/2} + T_{k4+N/4} + T_{k4+3N/4}]}{4} \quad (3)$$

$$T_{mean} = \frac{\sum_{k=0}^{N-1} T_k}{N} \quad (4)$$

and where:

T is a value of the blood temperature output signal;

k4 is an index, running from 0 to $N/4-1$, established over one quarter of the range of the measurement interval; and N is the number of samples of the blood temperature output signal used during an odd number of periods of the input signal.

The corrected output signal is then calculated in accordance with the following equation:

$$T_{corr_k} = T_k - (\text{Drift Slope}) \cdot \left[ k - \frac{N}{2} + 0.5 \right] - T_{mean} \quad (5)$$

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENTS

Figure 1:
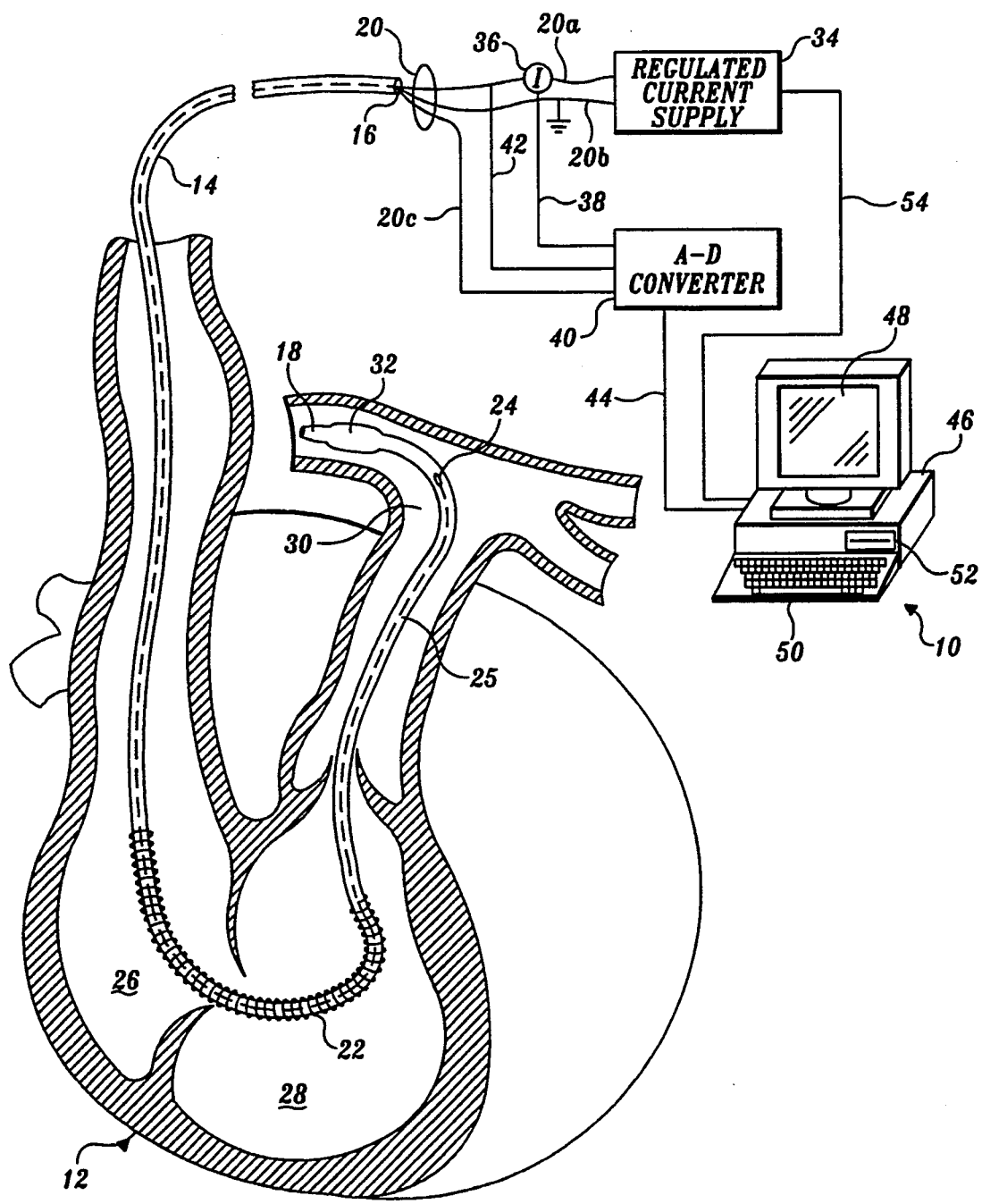
FIG. 1 is a block diagram of a first embodiment of the present invention illustrating the disposition of a catheter and electrical resistance heater within a human heart that is cut away to more clearly show the right auricle, ventricle and pulmonary artery.

A first embodiment of a cardiac output monitoring system in accordance with the present invention is shown generally in FIG. 1 at reference numeral 10. A human heart is schematically illustrated in this figure, with a portion of the heart cut away to show the disposition of a catheter 14 that is inserted through a patient's cardiovascular system and into heart 12. Catheter 14 has a proximal end 16 and a distal end 18. A plurality of leads 20 extend longitudinally through catheter 14 (within lumens that are not separately shown) and include leads 20a and 20b that carry an electrical current to an electrical resistance heater 22.

In the preferred form of the invention, heater 22 comprises a coil of insulated copper, stainless steel, nickel, or nichrome wire, approximately 12 centimeters in length that is wound around catheter 14 approximately 10 to 15 centimeters from distal end 18. Heater 22 has a nominal resistance of from 15 to 30 ohms. Leads 20c are connected to a temperature sensor 24, which is spaced apart from distal end 18 and generally mounted on the external surface of the catheter so that it can readily sense the temperature of blood flowing past the distal end as blood is pumped from heart 12. As shown clearly in FIG. 1, catheter 14 extends through a right auricle 26, a right ventricle 28, and into a pulmonary artery 30 of the patient whose cardiac output is being monitored. Adjacent distal end 18 is disposed a balloon 32, which is inflated to float distal end 18 upwardly, from right ventricle 28 into pulmonary artery 30. Heater 22 can be positioned entirely within right auricle 26 or, as shown, may extend from right auricle 26 into right ventricle 28.

A regulated current supply 34 supplies a periodic electrical current used to generate heat at heater 22, at a voltage ranging from 10 to 25 volts peak amplitude. The periodic electrical current can be supplied in a periodic sinusoidal waveform having either odd or even harmonics or both. Alternatively, a square wave current supply can be used. As the current flows through the wire coil comprising heater 22, it produces heat in proportion to the $I^2R$ losses in the heater (where I is the current and R is the resistance of the heater). The heat produced is transferred to the blood within right auricle 26 and right ventricle 28.

A current sensor 36 produces a signal indicative of the magnitude of the electrical current flowing through lead 20a to heater 22, and this signal is input through leads 38 to analog-to-digital (A-D) converters 40. A second input to A-D converters 40 is a voltage signal that indicates the voltage developed across heater 22; this voltage signal is conveyed by a lead 42. The third input to the A-D converters comprises the signal indicative of the temperature of the blood leaving heart 12, produced by temperature sensor 24, connected to leads 25, which comprise the distal end of leads 20c. Digital signals from A-D converters 40 are conveyed through leads 44 to input ports (not separately shown) on a portable computer 46.

Associated with portable computer 46 is a video display 48 on which data defining the cardiac output of heart 12 are displayed, along with other data and patient information. A keyboard 50 is connected to portable computer 46 to provide for input and user control of the cardiac output measurement. In addition, portable computer 46 includes a hard drive or floppy drive 52 that is used for magnetic storage of data, test results, and programs such as the software controlling the measurement of cardiac output. Portable computer 46 controls regulated current supply 34 by supplying control signals transmitted through leads 54 that extend between the regulated current supply and the portable computer.

Preferably, the electrical current that energizes heater 22 to heat the blood flowing through heart 12 is supplied either in the form of a sine wave having a 30 to 60 second period or a square wave with an energized period ranging between 15 and 30 seconds (followed by a like duration during which no current is supplied). The power developed by heater 22 thus represents a periodic input signal, whereas the signal developed by temperature sensor 24 comprises an output signal indicative of the temperature of the blood leaving the heart. To determine the power dissipated within heater 22, the digitized signals indicative of the current flowing through the heater and voltage drop across it are multiplied together by portable computer 46. The power dissipated within heater 22 to heat the blood flowing through heart 12, i.e., the amplitude, is therefore easily determined and is defined as the "input signal" for purposes of the following discussion. Accordingly, the power applied, which represents the input signal, and the temperature of the blood exiting the heart to the pulmonary artery, which represents the "output signal," are used in the preferred embodiment to determine the cardiac output of heart 12, as explained below.

An alternative embodiment of the method for developing an input signal and an output signal is to convey a cooling or heating fluid to a heat exchanger formed on the catheter in a manner known in the art. In either the preferred embodiment or the alternate embodiment, whether the input signal cools the blood or heats it, the cardiac output measurement system changes the temperature of blood in the heart on a periodic basis so that the output signal produced by the temperature sensor 24 changes periodically in response thereto.

As noted in the Background of the Invention, the present invention enables cardiac output to be determined continuously, rather than intermittently and is much less susceptible to noise than previous continuous cardiac output monitoring methods. In the present invention, cardiac output is determined by portable computer 46 following the logic steps shown in a flow chart 120 in FIG. 2. Starting at block 122, the temperature of blood flowing through heart 12 is modified by applying the input signal, e.g., by supplying electrical current to heater 22, or by conveying a cooling fluid through the catheter, thereby modifying the temperature of blood within the heart. The transfer of heat to or from blood within the heart 12 occurs at a frequency ω, as shown in block 122.

A dashed line block 124 indicates that the blood heated or cooled by the input signal mixes with the other blood in right ventricle 28 and enters pulmonary artery 30. A block 126 refers to temperature sensor 24, which produces the signal that is indicative of the temperature of blood exiting heart 12. With reference to block 128, the blood temperature T within pulmonary artery 30 comprises the output signal that is digitized by A-D converter 40.

In blocks 130–136, the output signal is corrected for thermal drift. As indicated in block 130, the average blood temperature $T_{mean}$ is determined by first summing the measured blood temperature T over one signal period. Since the output signal is sampled at N points, the average blood temperature over this time is determined in accordance with Equation 6 by dividing this sum by N.

$$T_{mean} = \frac{\sum_{k=0}^{N-1} T_k}{N} \qquad (6)$$

In block 132, a modified blood temperature output signal is produced by removing the odd and/or even harmonics in the output signal as explained below. In block 134, the drift slope of the modified output signal caused by thermal drift is determined, also as explained below. The drift slope and average blood temperature are then subtracted from the original output signal in block 136, thus removing the effects of thermal drift on the output signal. Subtracting $T_{mean}$ from the data in blocks 132 and 136 increases floating point numerical accuracy in these and subsequent calculations and is thus the preferred method. However, subtracting $T_{mean}$ is not essential for this drift removal technique to function, and all equations could be rewritten by deleting all $T_{mean}$ terms.

In the preferred embodiment, the slope of the output signal caused by thermal drift is determined using a least mean square fit (linear regression) algorithm. In order to produce accurate results with a least mean square fit algorithm, it is important that the portion of the signal being fitted does not contain any odd or even harmonics resulting from the input signal. Therefore, in the preferred embodiment, odd and even harmonics are removed from the output signal prior to determining the drift slope. It is also contemplated that an equivalent method can be used that is carded out in the frequency domain. In this alternative embodiment of the method, a discrete Fourier transform or a filtering operation is performed on the derived drift only signal to determine a drift only spectrum. The drift only spectrum is then subtracted from a spectrum of the output temperature signal, enabling the corrected output signal that results to be used in determining cardiac output, substantially independent of thermal drift.

Figure 3:
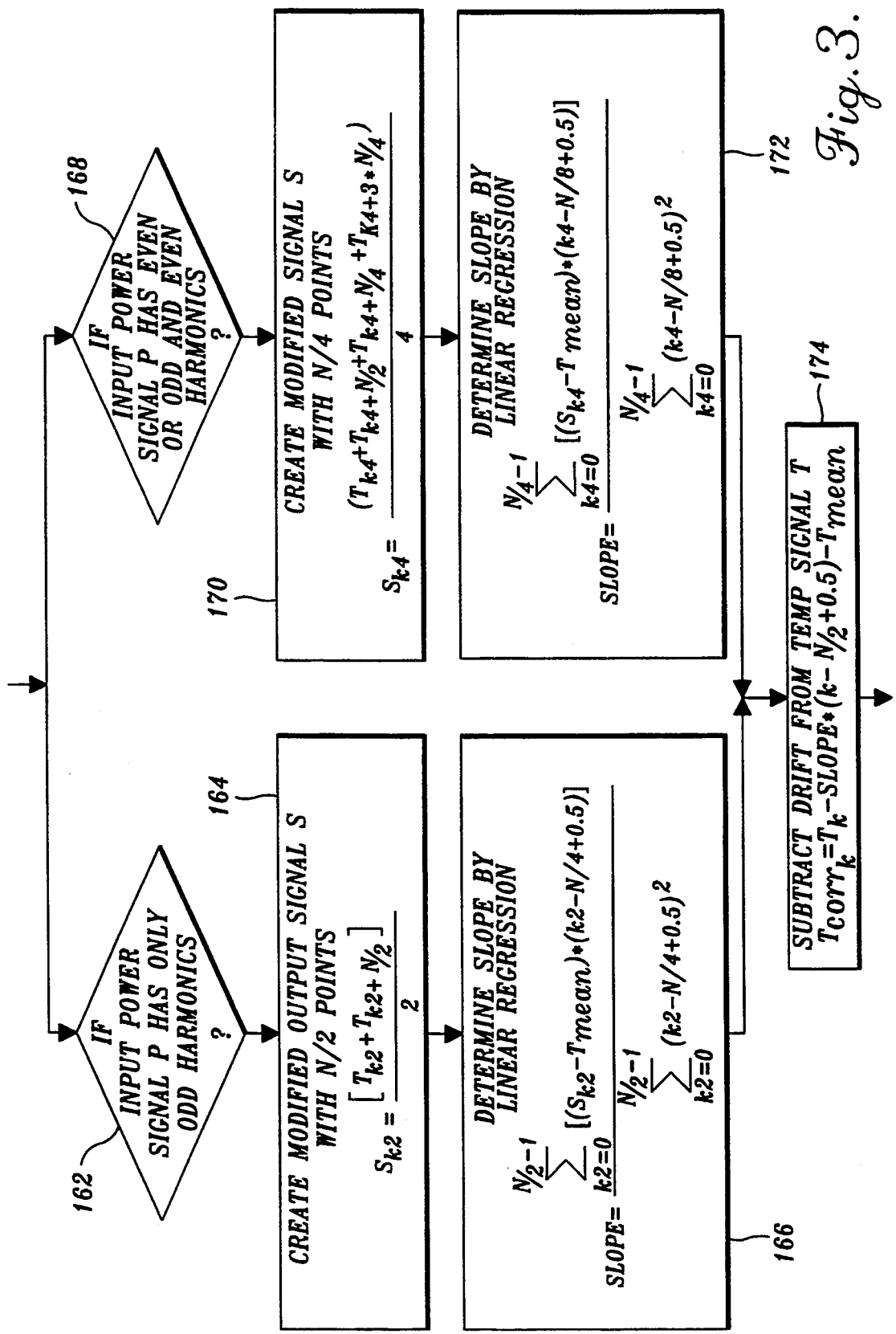
FIG. 3 is a flow chart showing the logical steps used in correcting the cardiac output for thermal drift.

In the embodiment shown in FIG. 3, if the input and thus output signal T contain only odd harmonics as indicated in block 162, a modified output signal S is created by establishing a new index k2 over half the range of the output signal period, i.e., with k2 going from 0 to (N/2−1). The output signal T would include only odd harmonics if, for example, the input signal comprises a square wave. In a block 164, the modified output signal $S_{k2}$ is created with k2 points from the average of the sum of the output signal at an interval of half the signal period in accordance with Equation 7, which follows below, thus removing the odd harmonics resulting from the input signal, but leaving the slope.

$$S_{k2} = \frac{[T_{k2} + T_{k2+N/2}]}{2} \quad (7)$$

The slope of the modified output signal $S_{k2}$ is then calculated in block 166 using a least mean squares fit (linear regression) algorithm in accordance with Equation 8:

$$SLOPE = \frac{\sum_{k2=0}^{N/2-1} [S_{k2} - T_{mean}] \cdot [k2 - N/4 + 0.5]}{\sum_{k2=0}^{N/2-1} [k2 - N/4 + 0.5]^2} \quad (8)$$

Equation 8 can alternatively be rewritten to account for the calculations used to produce the modified output signal as follows:

$$SLOPE = \quad (9)$$

$$\frac{\sum_{k2=0}^{N/2-1} [T_{k2} + T_{k2+\frac{N}{2}} - 2 \cdot T_{mean}] \cdot \left[k2 - \frac{N}{4} + 0.5\right]}{2 \cdot \sum_{k2=0}^{N/2-1} \left[k2 - \frac{N}{4} + 0.5\right]^2}$$

If the output signal has odd and even harmonics or even harmonics, as indicated in a block 168, the modified output signal is created by establishing a new index k4 over a quarter of the range of the signal period, k4=0, ..., (N/4−1). In a block 170, the modified output signal $S_{k4}$ is created with N/4 points from the average sum of the output signal at an interval of a quarter of the signal period in accordance with Equation 10, thus removing all odd (1,3,5,7 ...) and alternate even harmonics (2,6,10,14 ...) resulting from the input signal, but leaving the slope.

$$S_{k4} = \frac{[T_{k4} + T_{k4+N/2} + T_{k4+N/4} + T_{k4+3N/4}]}{4} \quad (10)$$

Similar to the case in which the output signal contained only odd harmonics, the slope of the modified output signal is determined in a block 172 using a least mean squares fit (linear regression) algorithm in accordance with Equation 11:

$$SLOPE = \frac{\sum_{k4=0}^{N/4-1} [S_{k4} - T_{mean}] \cdot \left[k4 - \frac{N}{8} + 0.5\right]}{\sum_{k4=0}^{N/4-1} \left[k4 - \frac{N}{8} + 0.5\right]^2} \quad (11)$$

Equation 11 can alternatively be rewritten to account for the calculation used to produce the modified output signal, in accordance with equation 12:

$$SLOPE = \frac{\sum_{k4=0}^{N/4-1} [T_{k4} + T_{k4+N/2} + T_{k4+N/4} + T_{k4+3N/4} - 4 \cdot T_{mean}] \cdot \left[k4 - \frac{N}{8} + 0.5\right]}{4 \cdot \sum_{k4=0}^{N/4-1} \left[k4 - \frac{N}{8} + 0.5\right]^2} \quad (12)$$

The method described above in connection with Equations 6 to 12 can be rewritten in terms of other equations in a completely general form to include all odd and any arbitrary number of even harmonics. A single parameter g (appearing below in Equation 14) determines the harmonics that are removed before linear regression is performed to identify drift slope. In choosing this parameter g, it is important that only the minimum number of even harmonics resulting from the input are removed, since the least square fitting operation is less accurate as a larger number of harmonics are removed.

The generalized form of the method used in Equations 6 to 12 is revealed in Equations 13 to 17. First, a modified output temperature signal $S_{kp}$, without any odd and even harmonics resulting from the input signal is created in accordance with Equation 13:

$$S_{kp} = \frac{\sum_{q=0}^{p-1} T_{(kp+\frac{q \cdot N}{p})}}{p} \quad (13)$$

where:

$$p = 2^g \quad (14)$$

To minimize the number of harmonics removed, g is an integer chosen such that the highest even harmonic in the output resulting from the input signal is less than or equal to (p−1). The value of p given by equation 14 is optimum where the trend is being removed from a single period of the input signal. A value for p less than that given by equation 14 can be used if trend is to be identified over more than one period of the input. The preferred method is to identify trends over a single period. The index kp is an index running from 0 to (N/p−1), where N is the number of samples of the blood temperature output signal T used during an integral number of periods of the input signal, usually one period. In S, the effects of all odd harmonics are eliminated, while the effects of even harmonics resulting from the input signal are eliminated up to the harmonic (p−1), leaving the effect of even harmonics p and integral multiples of p, i.e., p, 2p, 3p, ... etc. There were no harmonics p, 2p, 3p ... resulting from the input in T, so the slope of S and thus the drift slope of T is identified by linear regression in accordance with Equation 15:

$$\text{SLOPE} = \frac{\sum_{kp=0}^{N/p-1} [S_{kp} - T_{mean}] \cdot \left[ kp - \frac{N}{2 \cdot p} + 0.5 \right]}{\sum_{kp=0}^{N/p-1} \left[ kp - \frac{N}{2 \cdot p} + 0.5 \right]^2} \quad (15)$$

where the mean temperature for the N samples of T is calculated in accordance with equation 16:

$$T_{mean} = \frac{\sum_{k=0}^{N-1} T_k}{N} \quad (16)$$

Alternatively Equations 13 and 15 can be combined to obtain slope directly in accordance with equation 17:

$$\text{SLOPE} = \frac{\sum_{kp=0}^{N/p-1} \left[ \frac{\sum_{q=0}^{p-1} T_{(kp+\frac{q \cdot N}{p})}}{p} - T_{mean} \right] \cdot \left[ kp - \frac{N}{2 \cdot p} + 0.5 \right]}{\sum_{kp=0}^{N/p-1} \left[ kp - \frac{N}{2 \cdot p} + 0.5 \right]^2} \quad (17)$$

After determining the slope of the modified output signal caused by thermal drift, and thus the slope of the original output signal, the output signal is corrected in a block 174 FIG. 3, by subtracting the effects of thermal drift in accordance with Equation 18:

$$T_{corr_k} = T_k - \text{SLOPE} \cdot \left[ k - \frac{N}{2} + 0.5 \right] - T_{mean} \quad (18)$$

where $T_{corr_k}$ is the output signal corrected for the effects of thermal drift. The corrected output signal Tcorr is used to determine cardiac output as described below.

Figure 2:
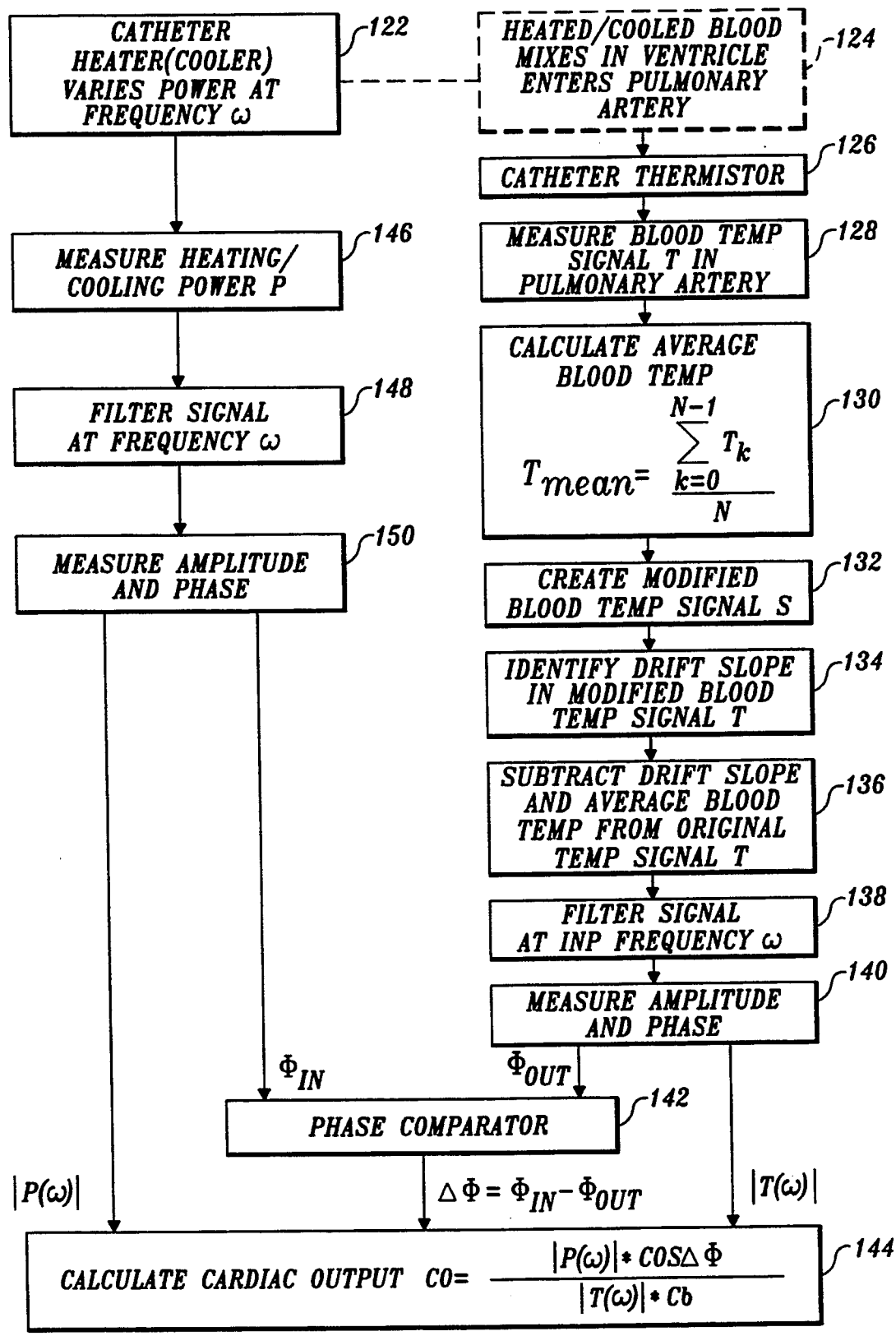
FIG. 2 is a flow chart showing the logical steps used in determining cardiac output in accordance with the present invention.

After the output signal indicative of the temperature of blood within the pulmonary artery is corrected for thermal drift, it is filtered at the input frequency $\omega$, as indicated in a block 138 in FIG. 2. In the preferred embodiment, the output signal is filtered by portable computer 46. Specifically, a discrete Fourier transform is performed on the digitized output signal to transform the signal from the time domain into the frequency domain. The portion of the transformed signal at the input frequency $\omega$ is thus determined and comprises a filtered output signal. By filtering the output signal (and the input signal, as described below), noise at other frequencies is substantially eliminated. Alternatively, an analog bandpass filter circuit could be used to process the input signal before it is digitized, in lieu of the discrete Fourier transform. Other types of digital or analog filtering could also be used to eliminate noise components at other frequencies.

After the output signal is filtered, the amplitude of the filtered output signal is determined, as noted in block 140. Portable computer 46 uses the peak-to-peak value of the filtered output signal for this amplitude, represented by $|T(\omega)|$. The value $|T(\omega)|$ is then used in a block 142 for calculating cardiac output. Since the filtered output signal is a periodically varying signal, it has a phase relationship that is represented by the value $\phi_{out}$ (used as described below).

The left side of flow chart 120 is directed to the steps used in processing the input signal. As shown in a block 146, the power P, which represents the heat transferred to the blood in the heart, is determined. As described above, the heating power of heater 22 is determined from the product of the electrical current flowing through it and the voltage drop across the heater, as well known to those of ordinary skill in the art.

Portable computer 46 then filters the input signal at the input frequency $\omega$, as indicated in a block 148. To filter the input signal, the portable computer processes it with a discrete Fourier transform, converting it from the time domain to the frequency domain. The portion of the transformed signal at the frequency $\omega$ comprises the filtered input signal, which has both a phase and an amplitude. In a block 150, the amplitude of the input signal is determined and is input to a block 144 as $|P(\omega)|$. The phase of this filtered input signal, $\phi_{in}$, is compared to the phase of the output signal in a block 142, producing a differential phase $\Delta\phi$, which is equal to the difference between $\phi_{in}$ and $\phi_{out}$. Portable computer 46 determines the differential phase and as shown in block 144, calculates cardiac output "CO" as follows:

$$CO = \frac{|P(\omega)| \cdot \cos(\Delta\Phi)}{(|T(\omega)| \cdot Cb)} \quad (19)$$

In the above equation 19, the value Cb is the product of specific heat and density of blood.

The volume of blood within right ventricle of heart 12, i.e., the mixing volume, is estimated from the following expression:

$$V = \frac{\tau \cdot |P(\omega)| \sqrt{\frac{1}{(\cos(\Delta\Phi))^2} - 1}}{2 \cdot \pi \cdot Cb \cdot |T(\omega)|} \quad (20)$$

where $\tau$ is the period of the input signal. To reduce the effects of phase noise on the determination of cardiac output, an estimation of mixing volume can be made from Equation 20 and used in the following relationship:

$$CO = \sqrt{\left(\frac{|P(\omega)|}{Cb \cdot |T(\omega)|}\right)^2 - (\omega \bar{V})^2} \quad (21)$$

The estimate of mixing volume is preferably averaged over a long term (assuming that volume is relatively constant over the time during which cardiac output is determined), yielding an average mixing volume, $\bar{V}$, which is used in Equation 21 to determine cardiac output. The resulting determination of cardiac output from Equation 21 is therefore less sensitive to phase noise, including heart rate variations.

When a heat signal is injected into the blood within heart 12, either by cooling the blood or by applying heat to it, a transport delay time is incurred before the input heat signal reaches temperature sensor 24 in the pulmonary artery. The transport delay time adds a phase shift that is flow rate and vessel size dependent. The phase error due to transport delay time is defined as:

$$\Delta\Phi_{error} = \frac{\pi \cdot R^2 \cdot \omega \cdot L}{1000 \cdot CO} \quad (22)$$

where
- L is equal to the length of the path from the point of which the heat signal is injected into the blood within the heart to the point at which the temperature sensor is disposed (in cm),
- R is the vessel radius (in cm), and
- CO is the cardiac output in liters/second. For example, a typical phase shift would be approximately 28.8° for a path 10 cm in length, a radius of 1.6 cm, with a rate of flow of one liter per minute, and a period for the injection of the heat signal equal to 60 seconds.

The phase shift introduced by transport delay becomes significant at relatively low flow rates, making accurate correction for the mixing volume difficult. One way to address this problem is to apply the input signal at two (or more) different frequencies, enabling a separate estimate of transport delay phase shift and mixing volume phase shift to be determined from the difference in phase shift at the different frequencies.

There are two additional sources of error for which corrections can be applied in determining cardiac output. The sources of error relate to the time constant for the catheter and thermistor caused by their respective thermal masses. The thermal mass of the catheter attenuates and phase shifts the input signal, whereas the thermal mass of temperature sensor 24 attenuates and phase shifts the received temperature signal corresponding to the change in temperature in the blood flowing past temperature sensor 24. The correction used in the preferred embodiment assumes a simple first-order system. For example, heater 22 is assumed to have a time constant $T_{htr}$ (actually the time constant is for the catheter and heater), and temperature sensor 24 to have a time constant $T_{sens}$, both of which are empirically determined. Cardiac output is then determined from:

$$CO = \frac{|P(\omega)| \cdot \cos(\Phi_{in} - \Phi_{out} - \Phi_{htr} - \Phi_{sens}) \cdot HTR_{atten} \cdot SENSOR_{atten}}{|T(\omega)| \cdot Cb} \quad (23)$$

where:
$\phi_{htr} = -\text{ARCTAN}(\omega \cdot T_{htr})$;
$\phi_{sens} = -\text{ARCTAN}(\omega \cdot T_{sens})$;
$HTR_{atten} = \cos(\phi_{htr})$; and
$SENSOR_{atten} = \cos(\phi_{sens})$.

Equation 23 recognizes that a time delay occurs between the arrival at temperature sensor 24 of blood having a different temperature due to the input of a heat signal and the change in the output signal of the temperature sensor. Similarly, the thermal mass of the catheter/heater introduces a time delay between the application of the input signal and the transfer of energy into the blood around heater 22 (or heat exchanger 60). Typical time constants for both heater 22 and temperature sensor 24 are approximately two seconds each. Based on the assumption that the time constants for these two elements do not vary with flow rate, amplitude errors and thus cardiac output errors introduced from this source of error should be constant, dependent only on the frequency of the input signal. Accordingly, the phase shift introduced by these time constants should also be constant. Since the sensitivity to phase errors increases at low flow rates and large mixing volumes, it is important to correct for the phase shift due to the time constants of the catheter/heater (or heat exchanger) and temperature sensor, at large overall phase angles. A number of applications of the basic slope identification method are possible, which fit a more complex curve through adjacent or overlapping measurement periods by identifying the (drift) slope of adjacent periods and then fitting a spline or higher order curve through the data using this slope information. Under high levels of noise, these techniques break down and couple poor curve fitting errors into multiple measurement periods, instead of improving accuracy. In addition, they increase measurement delay time.

Trend removal, as described above, is not limited to use with the specific cardiac output calculation disclosed, but can also be applied before carrying out the output calculation based upon almost any of the prior art continuous cardiac output measurement techniques, such as the technique described by Yelderman (U.S. Pat. No. 4,507,974) and Newbower (U.S. Pat. No. 4,236,527).

While the preferred embodiment of the invention has been illustrated and described, it will be appreciated that various changes can be made therein without departing from the spirit and scope of the invention. Accordingly, it is not intended that the scope of the present invention be in any way limited by the disclosure of the preferred embodiment, but instead that it be determined entirely by reference to the claims that follow.

The embodiments of the invention in which an exclusive property or privilege is claimed are defined as follows:

1. A method for determining a cardiac output of a heart with reduced dependence on thermal drift, comprising the steps of:
   (a) providing an input signal that changes a temperature of blood within the heart so that it varies periodically;
   (b) sensing a temperature of blood leaving the heart, producing a blood temperature output signal that varies periodically;
   (c) determining a drift slope of the blood temperature output signal due to thermal drift by filtering a portion of said blood temperature output signal that represents a change in the temperature of the blood caused by the input signal;
   (d) using the drift slope, producing a corrected output signal that is compensated for thermal drift; and
   (e) determining cardiac output as a function of the corrected output signal, said cardiac output thus determined having a reduced dependence on thermal drift.

2. The method of claim 1, wherein step (c) further comprises determining the drift slope by performing a least mean squares fit of said portion of said blood temperature output signal.

3. The method of claim 1, further comprising the step of producing a modified output signal, without odd and alternate even harmonics resulting from the input signal, as a function of the blood temperature output signal, wherein steps (c) and (d) comprise the steps of:
   (a) determining the drift slope of the modified output signal; and
   (b) producing the corrected output signal using the drift slope determined from the modified output signal.

4. The method of claim 3, wherein the modified output signal is produced without odd harmonics resulting from the input signal in accordance with:

$$S_{k2} = \frac{[T_{k2} + T_{k2+N/2}]}{2}$$

where:
$S_{k2}$ defines the modified output signal;
$k2$ is an index, running from 0 to $(N/2-1)$;
T is a value of the blood temperature output signal; and
N is the number of samples of the blood temperature output signal used during an odd number of periods of the input signal.

5. The method of claim 4, wherein the drift slope is defined by:

$$\text{Drift Slope} = \frac{\sum_{k2=0}^{N/2-1}[S_{k2} - T_{mean}] \cdot [k2 - N/4 + 0.5]}{\sum_{k2=0}^{N/2-1}[k2 - N/4 + 0.5]^2}$$

where:

$$T_{mean} = \frac{\sum_{k=0}^{N-1} T_k}{N}.$$

$T_k$ is a value of the blood temperature output signal;
k is an index, running from 0 to $(N-1)$.

6. The method of claim 3, wherein the modified output signal is produced without odd and alternate even harmonics resulting from the input signal, in accordance with the following equation:

$$S_{k4} = \frac{[T_{k4} + T_{k4+N/2} + T_{k4+N/4} + T_{k4+3N/4}]}{4}$$

where:
$S_{k4}$ defines the modified output signal;
$k4$ is an index, running from 0 to $(N/4-1)$;
T is a value of the blood temperature output signal; and
N is the number of samples of the blood temperature output signal used during an odd number of periods of the input signal.

7. The method of claim 6, wherein the drift slope is defined by:

$$\text{Drift Slope} = \frac{\sum_{k4=0}^{N/4-1}[S_{k4} - T_{mean}] \cdot \left[k4 - \frac{N}{8} + 0.5\right]}{\sum_{k4=0}^{N/4-1}\left[k4 - \frac{N}{8} + 0.5\right]^2}$$

where:

$$T_{mean} = \frac{\sum_{k=0}^{N-1} T_k}{N}$$

8. The method of claim 1, wherein the corrected output signal is produced by removing a trend in the blood temperature output signal caused by said drift slope.

9. The method of claim 5, wherein the corrected output signal, $Tcorr_k$, is defined by:

$$Tcorr_k = T_k - (\text{Drift Slope}) \cdot \left[k - \frac{N}{2} + 0.5\right] - T_{mean}$$

where:
$T_k$ is a $k_{th}$ value of the blood temperature output signal;

$$T_{mean} = \frac{\sum_{k=0}^{N-1} T_k}{N}; \text{ and}$$

N is the number of samples of the blood temperature output signal used during an odd number of periods of the input signal.

10. The method of claim 7, wherein the corrected output signal, $Tcorr_k$, is defined by:

$$Tcorr_k = T_k - (\text{Drift Slope}) \cdot \left[k - \frac{N}{2} + 0.5\right] - T_{mean}$$

where:
$T_k$ is a value of the blood temperature output signal;
k is an index from 0 to $(N-1)$;

$$T_{mean} = \frac{\sum_{k=0}^{N-1} T_k}{N} \text{; and}$$

N is the number of samples of the blood temperature output signal used during an odd number of periods of the input signal.

11. A method for determining a cardiac output of a heart with reduced dependence on thermal drift, comprising the steps of:
   (a) providing an input signal that changes a temperature of blood within the heart so that it varies periodically;
   (b) sensing a temperature of blood leaving the heart, producing a blood temperature output signal that varies periodically;
   (c) using the blood temperature output signal, producing a corresponding output signal in the frequency domain;
   (d) producing a frequency spectrum due to thermal drift using the corresponding output signal in the frequency domain; and
   (e) subtracting the frequency spectrum due to thermal drift from the corresponding output signal in the frequency domain, thereby producing a corrected output signal that is compensated for thermal drift.

12. Apparatus for determining a cardiac output of a heart with reduced dependence on thermal drift, comprising:
   (a) a catheter that is insertable into a heart through a cardiovascular system, having a distal end;
   (b) means for supplying a periodically varying, temperature modifying input signal to a portion of the catheter inserted into the heart;
   (c) a blood temperature sensor disposed adjacent to the distal end of the catheter, said temperature sensor being provided to produce a blood temperature output signal that is indicative of a temperature of blood flowing from the heart;
   (d) means for determining a drift slope of the blood temperature output signal caused by thermal drift, by filtering a portion of said blood temperature output signal that represents a change in the temperature of the blood caused by the input signal;
   (e) means for producing a corrected blood temperature output signal compensated for thermal drift using the drift slope; and
   (f) control means for determining the cardiac output of the heart as a function of said corrected blood temperature output signal, said cardiac output thus determined having a reduced dependence on thermal drift.

13. The apparatus of claim 12, wherein the means for determining the drift slope comprise means for performing a least mean squares fit of the blood temperature signal.

14. The apparatus of claim 12, further comprising means for producing a modified output signal without odd and alternate even harmonics caused by the input signal.

15. The apparatus of claim 14, wherein the means for producing a modified output signal from the blood temperature output signal, derived without odd harmonics caused by the input signal, determines the modified signal in accordance with the following:

$$S_{k2} = \frac{[T_{k2} + T_{k2+N/2}]}{2}$$

where:
   $S_{k2}$ is the modified output signal;
   k2 is an index, running from 0 to $N/2-1$;
   T is a value of the blood temperature output signal; and
   N is the number of samples of the blood temperature output signal used during an odd number of periods of the input signal.

16. The apparatus of claim 15, wherein the drift slope is defined as follows:

$$\text{Drift Slope} = \frac{\sum_{k2=0}^{N/2-1} [S_{k2} - T_{mean}] \cdot [k2 - N/4 + 0.5]}{\sum_{k2=0}^{N/2-1} [k2 - N/4 + 0.5]^2}$$

where:

$$T_{mean} = \frac{\sum_{k=0}^{N-1} T_k}{N}.$$

17. The apparatus of claim 14 wherein the modified output signal $S_{k4}$ is derived from the blood temperature output signal, without odd and alternate even harmonics resulting from the input signal, in accordance with the following:

$$S_{k4} = \frac{[T_{k4} + T_{k4+N/2} + T_{k4+N/4} + T_{k4+3N/4}]}{4}$$

where:
   $S_{k4}$ defines the modified output signal;
   k4 is an index, running from 0 to $(N/4-1)$;
   T is a value of the blood temperature output signal; and
   N is the number of samples of the blood temperature output signal used during an odd number of periods of the input signal.

18. The apparatus of claim 17, wherein the drift slope is defined by:

$$\text{Drift Slope} = \frac{\sum_{k4=0}^{N/4-1} [S_{k4} - T_{mean}] \cdot \left[k4 - \frac{N}{8} + 0.5\right]}{\sum_{k4=0}^{N/4-1} \left[k4 - \frac{N}{8} + 0.5\right]^2}$$

where:

$$T_{mean} = \frac{\sum_{k=0}^{N-1} T_k}{N}$$

19. The apparatus of claim 16, wherein the corrected blood temperature output signal, $Tcorr_k$, is defined as follows:

$$Tcorr_k = T_k - (\text{Drift Slope}) \cdot \left[k - \frac{N}{2} + 0.5\right] - T_{mean}$$

where:
   $T_k$ is a value of the blood temperature output signal;

k is an index from 0 to (N−1);

$$T_{mean} = \frac{\sum_{k=0}^{N-1} T_k}{N} ; \text{ and}$$

N is the number of samples of the blood temperature output signal used during an odd number of periods of the input signal.

20. The apparatus of claim 18, wherein the corrected blood temperature output signal, $Tcorr_k$, is defined as follows:

$$Tcorr_k = T_k - (\text{Drift Slope}) \cdot \left[ k - \frac{N}{2} + 0.5 \right] - T_{mean}$$

where:
$T_k$ is a value of the blood temperature output signal; and
k is an index from 0 to (N−1);

$$T_{mean} = \frac{\sum_{k=0}^{N-1} T_k}{N} .$$

21. The apparatus of claim 12, further comprising means for producing a modified output signal $S_{kp}$ without any odd and even harmonics resulting from the input signal, in accordance with the following:

$$S_{kp} = \frac{\sum_{q=0}^{p-1} T_{(kp + \frac{q \cdot N}{p})}}{p}$$

where:
$S_{kp}$ defines the modified output signal;
kp is a new index, running from 0 to (N/(p−1));
T is a value of the blood temperature output signal;
N is the number of samples of the blood temperature output signal used during an integral number of periods of the input signal, greater than 0; and
p is an integer chosen to eliminate all harmonics of the output signal resulting from the input signal, for a single period input signal, p=2$^g$ where g is an integer such that the highest even harmonic of the output signal resulting from the input signal is less than or equal to (p−1).

22. The apparatus of claim 21, wherein the drift slope is defined by:

$$\text{Drift Slope} = \frac{\sum_{kp=0}^{N/p-1} [S_{kp} - T_{mean}] \cdot \left[ kp - \frac{N}{2 \cdot p} + 0.5 \right]}{\sum_{kp=0}^{N/p-1} \left[ kp - \frac{N}{2 \cdot p} + 0.5 \right]^2}$$

where:

$$T_{mean} = \frac{\sum_{k=0}^{N-1} T_k}{N} .$$

23. The apparatus of claim 22, wherein the corrected blood temperature output signal, $Tcorr_k$, is defined as follows:

$$Tcorr_k = T_k - (\text{Drift Slope}) \cdot \left[ k - \frac{N}{2} + 0.5 \right] - T_{mean}.$$

24. The apparatus of claim 12, wherein the drift slope is defined by:

Drift Slope =

$$\frac{\sum_{kp=0}^{N/p-1} \left[ \frac{\sum_{q=0}^{p-1} T_{(kp + \frac{q \cdot N}{p})}}{p} - T_{mean} \right] \cdot \left[ kp - \frac{N}{2 \cdot p} + 0.5 \right]}{\sum_{kp=0}^{N/p-1} \left[ kp - \frac{N}{2 \cdot p} + 0.5 \right]^2}$$

where:

$$T_{mean} = \frac{\sum_{k=0}^{N-1} T_k}{N} ;$$

$S_{kp}$ defines a modified output signal;
kp is a new index, running from 0 to (N/(p−1));
T is a value of the blood temperature output signal; and
N is the number of samples of the blood temperature output signal used during an integral number of periods of the input signal, greater than 0; and
p is an integer chosen to eliminate all harmonics of the output signal resulting from the input signal, for a single period input signal, p=2$^g$ where g is an integer chosen such that the highest even harmonic of the output signal resulting from the input signal is less than or equal to (p−1).

25. The apparatus of claim 24, wherein the corrected blood temperature output signal, $Tcorr_k$, is defined as follows:

$$Tcorr_k = T_k - (\text{Drift Slope}) \cdot \left[ k - \frac{N}{2} + 0.5 \right] - T_{mean}$$

where:
T is value of the blood temperature output signal;
k is an index from 0 to (N−1);

$$T_{mean} = \frac{\sum_{k=0}^{N-1} T_k}{N} ; \text{ and}$$

N is the number of samples of the blood temperature output signal used during an odd number of complete periods of the input signal.

* * * * *